United States Patent [19]

Eckert

[11] Patent Number: 4,537,713

[45] Date of Patent: Aug. 27, 1985

[54] PROCESS FOR THE REDUCTION OF REDUCIBLE GROUPS AND ITS USE

[76] Inventor: Heiner Eckert, Lerchenauerstrasse 9, 8000 München 40, Fed. Rep. of Germany

[21] Appl. No.: 379,789

[22] Filed: May 19, 1982

[30] Foreign Application Priority Data

May 29, 1981 [DE] Fed. Rep. of Germany ....... 3121478

[51] Int. Cl.$^3$ .................. C07C 103/52; C07C 101/00; C07C 69/76; C07C 63/04; C07C 101/04; C11C 3/12; C07D 265/30; C07D 215/04

[52] U.S. Cl. .............................. 260/112.5 R; 564/305; 564/416; 560/19; 560/105; 260/409; 260/245.81; 260/245.82; 260/245.83; 260/245.86; 562/493; 562/575; 544/178; 546/181

[58] Field of Search ..................... 260/245.86, 112.5 R, 260/409, 245.81, 245.83, 245.82; 564/416, 305; 560/19, 108; 562/493, 575; 546/181

[56] References Cited

U.S. PATENT DOCUMENTS

| | | | |
|---|---|---|---|
| 4,113,713 | 9/1978 | Schlatter et al. | 260/112.5 R |
| 4,250,086 | 2/1981 | Heavner | 260/112.5 R |
| 4,256,670 | 3/1981 | Homeier | 564/416 |
| 4,372,893 | 2/1983 | Eckert | 260/245.86 |

OTHER PUBLICATIONS

Angew. Chem. Internat., Edit. 11, No. 3, 159–248.
Chem. Abstr. 95, (1981), 79336g.
Chem. Abstr., vol. 99, (1983), 21589h.
Chem. Abstr., vol. 90, (1979), 204485e.
Chem. Abstr., vol. 88, (1978), 121692c and 61674m.
Chem. Abstr., vol. 86, (1977), 5792v.
Chem. Abstr., vol. 89, (1978), 24778y.

Primary Examiner—Delbert R. Phillips
Attorney, Agent, or Firm—Brooks Haidt Haffner & Delahunty

[57] ABSTRACT

The invention concerns a process for the reduction of groups containing unsaturated C,C—, C,N—,N,N—,N-,O— bonds, especially of $NO_2$—,NO—,NOH—,N-R—,CN—,$N_3$—,$N_2$-groups or C≡C or C-halogen- or acyl groups with hydrogen on MPc or with a suitable reduction agent on [MPc]$^\ominus$, whereby a platinum metal-phthalocyanine is used as the catalyst. It is possible that by the reversible change (control) of the oxidation phase z of the platinum metal from $z \geq 2$ to $z \leq 1$ using the same MPc complex, basically different reductions can be selectively catalysed.

Thus the invention concerns a process for selective reduction using platinum metal-phthalocyanine catalysts with reaction specificity in three different reaction patterns.

The inventive process is suitable, especially for the synthesis of α-phenylalkylamines, benzylalkylamines, N-alkyl-amino carboxylic acids, α-hydroxycarboxylic acids, peptides, N-heterocyclic compounds as well as generally in the field of pharmaceutical, herbicide and insecticide production.

25 Claims, No Drawings

PROCESS FOR THE REDUCTION OF REDUCIBLE GROUPS AND ITS USE

The process of this invention concerns the reduction of reducible groups, which contain unsaturated C,C—, C,N—, N,N—, N,O— bonds, especially $NO_2$—, NO—, NOH—, NR—, CN—, $N_3$—, $N_2$—, groups or C≡C, or C-halogen- or acyl groups with hydrogen over MPc or with a suitable reducing agent over $[MPc]^{\ominus}$.

In the literature processes for the reduction of e.g. nitro-compounds, nitriles or C═C double compounds are described. Please note the statements in patent application No. P 30 12 674.

The conventional heterogeneous hydrogenating catalysts such as the platinum metals or structure catalysts (Raney-Ni, Raney-Co, etc.) such as are described in "P. N. Rylander: Catalytic Hydrogenation over Platinum Metals" Academic Press, N.Y. 1967, have poor selectivity in reduction reactions which is caused by their ill-defined structure. A modification of these catalysts is only possible by purely empirical means by the adherence to very definite reaction conditions and/or the partial contamination of the catalysts and is therefore connected with great uncertainties as regards the attainment of a definite aim and the reproducibility of the results.

Hydrogenation of metal macrocycles were undertaken e.g. of (pyridine) cobaloxim (II) as has been described by R. Miyagawa, T. Yamaguchi, in "Nippon Kagaku Kaishi" 1978, pages 160 et seq. But the cobaloximes, like most of the vitamin $B_{12}$ complexes, have a tendency to decompose and tend to secondary reactions on the ligands. U.S. Pat. No. 4,256,670 describes a process for the preparation of amino-substituted aromatic compounds, by the reduction of the corresponding nitro-compounds at increased temperature and pressure. The catalysts used are metal-phthalocyanine complexes whereby the metals belong to group VIII of the periodic system. The reduction reactions of the above publication are carried out at pressures of 5 to 5000 atmospheres in autoclaves in the absence of a reduction agent. Because of the high temperature and pressure conditions the process is hard to perform according to the above publication for technical laboratory reasons. Moreover under the named conditions it is not possible to attain a selectivity of the reduction, i.e. due to the choice of the metal valency contained in the phthalocyanine complexes as well as the adjustment of the pH value, there is a reduction of certain groups, while other groups remain intact on the molecule.

It is the object of the present invention to make available a process which makes possible the reduction of unsaturated C,C, C,N—, N,N—, N,O— bonds as well as of C═C, or C-halogen or acyl groups, and in particular it is the object of the invention to make available a process which makes possible the selective reduction of a certain group apart from other reducible groups.

This object is attained by a process of the type named above which is characterized in that for the optionally selective reduction a platinum metal-phthalo-cyanine of the following formula is used as the catalyst:

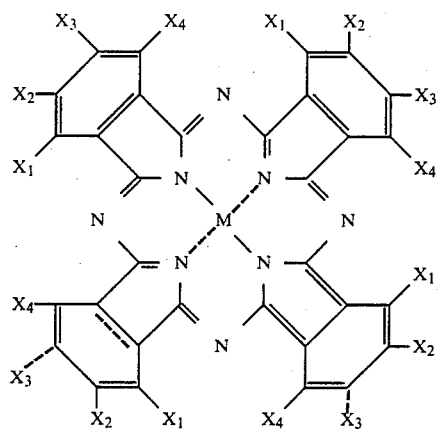

where M is a metal of the platinum series, $X^{1\text{-}4}H$ is halogen, cyano or optionally other substituents with the —I— effect, alkyl or aryl, whereby $X^{2\text{-}3}$ can also be components of the annelated ring system or poly-Pc structure and $X^{1\text{-}4}$ can independently substitute one or more of the benzoide rings.

The inventive platinum metal phthalocyanines (MPc) are thermally, chemically and photochemically extremely stable, and have a defined structure in contrast to the usual hydrogenation catalysts such as the platinum metals and the structural catalysts. The MPc therefore offer great opportunities for graduated modification such as for example the change of the stereochemistry on the Pc ligands by the introduction of substituents and or polymer Pc structures and/or variations of the metal M. In addition the MPc catalysed reductions proceed under very mild reaction conditions, to which we shall refer later in detail. The MPc thus constitute a new type of hydrogenation catalyst which combines the advantages of the above-mentioned two types (stability or a defined structure) without having their disadvantages (difficulty of modification or of decomposition).

The inventive catalyst is a phthalocyanine complex having a metal from the range of platinum metals such as Ru Os, Rh, Ir, Pd and Pt. The use of palladium-phthalocyanine catalysts is especially preferred.

Suitable reducing agents when using MPc are hydrogen or when using $[MPc]^{\ominus}NaBH_4$, Li $AlH_4$ or Na/Hg. Among the latter the use of $NaBH_4$ is particularly preferred.

MPc complexes are used as bifunctional reaction catalysts with controllable reaction specificity. Due to their controllable bifunctionally they are especially suitable for selective reduction. This will be shown by the comparison below of items (1) and (2).

(1) Reduction with hydrogen on $M^zPc$ ($z \geq 2$) is greatly pH-dependent and allows selective reduction depending on whether the reaction is carried out in a neutral or an acidic milieu or in a basic milieu.

(A) The following are reduced in a neutral or acidic milieu: aromatic nitro compounds, azomethine, enamine, aromatic aldehydes, olefins, alkines, furane, benzyl ester. The reduction of benzyl ester takes place preferably on a carboxylic acid against carbamic acid so that in this way a carboxylic acid benzyl ester can selectively be split off from a carbamic acid benzyl ester.

In the above reduction reaction the following remain intact: aromates (except for furane), aromatic halides, alkyl halides, acyl halides, carboxylic acids, carboxylic acid esters and -amides, nitriles, aliphatic aldehydes, benzyl ethers, -amines, and -amides, alkyl cyclopropane.

(B) The following are reduced in a basic milieu: aromatic compounds of nitrogen, azomethines, enamines, olefins, alkines, benzyl esters, aromatic halides, (fast)

The hydrogenation of β-pinene is stereoselective; 71% cis-pinane and 29% trans-pinane are formed.

In the above process the following remain intact: the aromates, alkyl halides, carboxylic acids, carboxylic acid esters and -amides, nitriles, benzyl ethers, -amines and -amides.

The pH dependent reaction specificity is so strongly marked that in the hydrogenation of p-chloronitrobenzene on PdPc at 20° C., 92% of aniline is received while on the addition of HCl 73% p-chloroaniline is isolated.

(2) Reduction with NaBH$_4$ (or partially also with NaHg) on M$^z$Pc (z≦1) takes place in a basic milieu; the following are reduced: aromatic and aliphatic nitro compounds, oximes, azomethine, enamine, nitriles, olefins, acetylene, alkyl halides; in addition a reductive fragmentation of fragmentable compounds such as β-halogen alkyl radical takes place In this process the following remain intact: aromates, aromatic halides, carboxylic acids, carboxylic acid esters and -amides, cyclopropylcarbonyl compounds.

M$^z$Pc catalysed reductions differ depending on z mainly in that where z≧2 especially the alkylhalides, nitriles and aliphatic nitro-compounds remain intact, while the aryl halides are rapidly hydrogenolysed with the addition of a base and where z≦1 aliphatic nitro-compounds react with reduction and alkyl halides react very rapidly with hydrogenolysis or fragmentation whereas aryl halides remain wholly intact.

The controllable reaction specificity of the MPc catalyst is so great that the reduction catalysis of TCBOC-Val-OBzL on Pd$^{II}$Pd with H$_2$ according to (1A) delivers 85% TCBOC-Val-OH, while on [Pd$^I$Pc]$^⊖$ with NaBH$_4$ according to (2), 81% H-Val-OBzL is produced. By contrast it has been observed that the TCBOC radical in the Pd/C catalysed reduction is almost wholly decomposed (decomposition product >80%).

The reaction is normally carried out under a protective gas or under the shield of the gas developed by the reaction. Moreover the platinum metal phthalocyanines as catalysts have the advantage against other hydrogenation catalysts such as Raney-Ni or palladium on carbon inter alia that they are not combustible in air even in a mixture with hydrogen.

Further they do not have to be produced immediately before the reaction, like Raney-Ni, and can be stored for unlimited periods without adherence to special storage conditions.

As the solvents all the polar solvents which do not carry any reducible groups can be used, preferably alcohols and alcohol-water mixtures, especially MeOH, EtOH, tert. BuOH/H$_2$O. In the alcohol/water mixtures the ratio of alcohol to water is about 10:1.

The reaction is carried out at a temperature of 0 to 200 degrees C., preferably from 0° to 50° C., and especially from 0° to 25° C. It is especially preferred to work when using H$_2$ as the reducing agent in a low temperature range without pressure.

The concentration of the catalyst used can amount in the lower range to 0.001M. Preferably a catalyst concentration of 0.01 to 0.05M is used.

The substrate concentration, i.e. the concentration of the compound to be reduced can amount to up to 10M, preferably 0.1 to 2M.

As stated above the reduction can be greatly accelerated by the additional use of a free base. For this purpose the primary, secondary or tertiary amines, phosphines, or arsines, preferably the secondary or tertiary amines, are specially suitable, whereby triethylamine is particularly preferred. The reduction speed in general increases by a factor ≧2 and during the dehalogenation of arylhalides by a factor ≧200.

The table 1 below shows the selectivity of the reductions catalysed with the palladium-phthalocyanine complex with hydrogen. The table reflects the pH dependence of the reactions, while the reduction in the first case was carried out in an approximately neutral medium and in the second case with the addition of a tertiary base.

The inventive process is specially suitable for the carrying out a selective reduction reactions in the presence of:

1. an acidic halide group, whereby the latter remains intact during reduction catalysis with H$_2$;
2. an optionally geminal polyhalogenated alkyl halide group, whereby the latter remains intact during reduction with H$_2$;
3. a benzyl amine- or 1-ferrocenylalkylamino group, maintaining the latter;
4. a benzyl ether- or 1-ferrocenyl-alkylether group, maintaining the latter;
5. a benzyl amide- or 1-ferrocenylalkalamide group, maintaining the latter.

In addition, by means of the inventive process optionally substituted benzyl- or benzyloxycarbonyl groups can also be selectively split off apart from and maintaining easily reducible aromates or heteroaromates. Moreover when using the inventive process the optionally substituted benzyl ester group is also selectively hydrogenolysed apart from and maintaining optionally geminal polyhalogenated alkylhalide groups, especially the 2,2,2-trichlorotert.-benzyloxy carbonyl radicals.

The inventive process is also suitable for splitting off β-halogen-alkyl radicals, especially the 2,2,2-trichloro-tert.-butyl radicals and the 2,2,2-trichloro-tert.-butyloxy carbonyl radical by the reductive fragmentation with NaBH$_4$ selectively from heteroatoms such as O, N or S. This also applies to the splitting off of β-halogenalkyl radicals and the 2,2,2-trichloro-tert.-butyloxycarbonyl radicals, selectively in the presence of a benzyl ester.

It is of special significance that by the use of the inventive process during the MPc catalysed reduction reactions with H$_2$ aromatic halides can by the suitable choice of the pH value optionally by the addition of a base, or by adding an acidic additive they remain intact without thereby the reduction reactions of another functional group being meaningfully adversely affected.

TABLE 1

Selectivity of PdPc catalysed reductions with H$_2$ of functional groups (depending on pH value)

| Functional group | Product after reaction with | |
|---|---|---|
| | H$_2$/PdPc | H$_2$/PdPc/tert. base |
| NO$_2$ aromatic | NH$_2$ | NH$_2$ |
| NO$_2$ aliphatic | NO$_2$ | — |
| C≡N | C≡N | C≡N |
| C=N | CH—NH | CH—NH |
| CH=O aliphatic | CH=O | — |
| CH=O aromatic | CH$_3$[1] | — |

TABLE 1-continued

Selectivity of PdPc catalysed reductions with $H_2$ of functional groups (depending on pH value)

| Functional group | Product after reaction with | |
|---|---|---|
| | $H_2/PdPc$ | $H_2/PdPc$/tert. base |
| C=O aromatic | C=O | — |
| $CO_2R$ aromatic, aliphatic | $CO_2R$ | $CO_2R$ |
| $CONR_2$ aromatic, aliphatic | $CONR_2$ | $CONR_2$ |
| COCl aromatic, apliphatic | COCl | — |
| C=C conjugated, isolated | CH—CH | CH—CH |
| Hal aromatic | Hal | H |
| Hal aliphatic | Hal | Hal[2] |
| $CO_2$—Benzyl | $CO_2H$ | $CO_2^{\ominus}$ |
| CON—Benzyl | CON—Benzyl | CON—Benzyl |
| O—Benzyl | O—Benzyl | O—Benzyl |
| N—Benzyl | N—Benzyl | N—Benzyl |
| C=O (aromatic,aliphatic) +$NH_2$—R | CH—NH—R | CH—NH—R |
| R = H, Alkyl | | |

$$\underset{R'}{\overset{R}{\underset{|}{\vphantom{|}}}}\!\!\!\!\begin{matrix}R^1\\|\\-C=O\\|\\NO_2\end{matrix} \quad + \quad \begin{matrix}R^2\\|\\CH_2\\|\\O=C-R^{3'}\end{matrix} \quad \xrightarrow{} \quad \begin{matrix}R^1\\R\diagup\!\!\diagdown\!\!R^2\\|\quad\quad\|\\R'\diagdown\!\!\diagup\!\!R^3\\N\end{matrix} \qquad 3$$

Notes for Table 1:
[1] slow
[2] or alkylation product.
[3] R and R' together form any aromatic system. The $R^1C=O$ group on the aromatic system and the $NO_2$ group can be in any position in relation to each other, e.g. in the ortho- or the meta-positions. $R^1$, $R^2$ and $R^3$ are H, alkyl, aryl etc. Where $R^2$ = alkyl or aryl an additional carbonyl group can be present to activate a methylene group. By condensation, depending on the initial compounds a corresponding multi-membered heterocyclical ring system is formed.

The inventive process is suitable for optionally selective reduction using a platinum metal-phthalocyanine catalyst especially for the synthesis of α-phenyl alkylamines whereby the starting point can be the easily available aromatic ketones and ammonia or alkylamines. In addition the reduction process is used for the synthesis of benzyl-alkylamines, starting from easily available aromatic aldehydes and alkylamines.

The inventive process is specially used for the synthesis of N-alkylaminocarboxylic acids, especially N-alkyl-α-aminocarboxylic acids starting from the easily available α-ketocarboxylic acids and alkylamines. It is also suitable for the synthesis of α-hydroxycarboxylic acids, whereby the starting products are the easily available α-ketocarboxylic acids.

The inventive process is used especially in the synthesis of peptides, whereby the initial materials are N-terminal and C-terminal protected aminoacids or oligo- and polypeptides. The 2,2,2-trichloro-tert.-butyloxycarbonyl radical is especially suitable as the N-terminal protective group. A benzyl radical is preferably used as the C-terminal protective group.

The inventive process is preferably used in that:
1. the optionally substituted benzyl- or benzyloxycarbonyl groups of peptides which contain aromatic groups such as especially the aminoacids histidine, trytophane, tyrosine, phenylglycin, p-hydroxyphenylglycin, or phenylalanine, are hydrogenolytically separated or split off;
2. the aminoacids or oligo- and polypeptides or aminofunctions are protected by 2,2,2-trichloro-tert.-butyloxycarbonyl radicals and by benzyl radicals on the carboxyl functions;
3. in the selective separation of β-halogenalkyl radicals, especially of the 2,2,2-trichloro-tert.-butyloxycarbonyl radical with $NaBH_4$ on $[Pd^{I}Pc]^{\ominus}$ or of optionally substituted benzyl- or benzyloxycarbonyl radicals with $H_2$ on $Pd^{II}Pc$, secondary or teriary 1-ferrocenylalkylamide groups are maintained.

In addition the inventive process is preferably used for the preparation of the hexapeptide His-His-Trp-His-Trp-His, for the synthesis of N-heterocyclic compounds, starting with easily available primary amines and dialdehydes and/or diketones, and for the synthesis of N-mono-substituted alkylpiperazines, starting with easily available primary amines and 3-azaglutardialdehyde, the aminofunction of which is protected reversibly, preferably by a 2,2,2-trichloro-tert.-butyloxycarbonyl radical.

In addition the inventive reduction process is suitable for the synthesis of heterocyclic compounds, whereby the starting materials may be easily available nitro- or nitrosocompounds.

The inventive process is specially suited for the synthesis of pharmaceuticals, herbicides and insecticides, as well as of their intermediate products in which apart from amino groupings there are easily reducible groups, especially aromatic halogen and/or formyl.

EMBODIMENTS 1 TO 65

(a) General working rules for platinum metal-phthalocyanine catalysed reduction with hydrogen.

10 mMol educt or educts is/are dissolved in 5 ml solvent and with 0.1 mMol Mpc(PdPc=60 mg) and are stirred or shaken strongly with additives as an option. If it is not fully soluble up to 20 ml of solvent are used or the work is done in a suspension (tests no. 4 to 9, 24, 26, 30, 31, 49 to 63).

After saturation of the reaction mixture with $H_2$ reaction is caused until hydrogen uptake is ended or greatly reduced. For the reaction times please see the tables below. Then the catalyst is removed from the reaction mixtures which contain the product as salt, by filtration and washing out with a suitable solvent or solvent mixtures such as $EtOH/H_2O$ 1:1. From the reaction mixtures which contain the neutral, acidic or basic product not as a salt, the catalyst is obtained by the removal of the polar solvent (usually a volatile alcohol such as EtOH). The acceptance of the residue is performed in a solvent or solvent mixture which is nonpolar as far as possible such as ether. Then filtering off takes place via a layer 2-5 cm thick of $Na_2SO_4$ which retains the catalyst quantitatively and at the same time frees the solution of water, i.e. reaction water. Solutions which contain strongly basic products such as aliphatic amines are filtered using inert gas such as e.g. nitrogen. From the filter residue the catalyst is regained by quantitatively by the extraction of the $Na_2SO_4$ with $H_2O$, washing with $H_2O$ and drying at 20° to 200° C.

If the products are present as dissolved salts, they are released from the filtrate washed with ether with acids, such as hydrochloric acid, or bases such as sodium hydroxide solution, and are extracted with a nonpolar solvent or solvent mixture such as ether. After the concentration of the organic phase the product is obtained.

(b) Example 55a

To 880 mg (10 mMol) of pyruvic acid in 2 ml methanol is added by drops while stirring strongly a solution of 560 mg (10 mMol) KOH in 5 ml methanol (while cooling) and is compounded with 2 ml (20 mMol) n-butylamine and 60 mg (0.1 mMol) PdPc. The reaction mixture is saturated with $H_2$ and stirred while supplying $H_2$ from a gas burette 136h at 40° to 50° C. Then the mixture is concentrated, the residue taken up in water and PdPc is filtered off. The filtrate is washed with ether, concentrated and the residue is dried in a vacuum over KOH whereby 960 mg (66%) N-n-butyl-D,L-alanine potassium salt remain.

(c) Example 55b 151 g (10 mMol) o-nitrobenzaldehyde are dissolved in 5 ml methanol and 1.2 ml (12 mMol) 10N HCl (while cooling) 5 ml acetone and 60 mg (0.1 mMol) PdPc added. The reaction mixture is saturated with $H_2$ and stirred while supplying $H_2$ from a gas burette 120 h at 55°-60° C. Then the PdPc is filtered off and the filtrate is divided into water and hexane. The water phase is alkalized with NaOH, extracted three times with ether, the ether phase is dried over KOH, and concentrated whereby 610 mg (43%) 2-methyl quinoline remain.

Moreover it is possible to carry out the reaction with a compound which contains substituted in the aromatic ring one or more substituents such as halide, especially chloride, nitrile, carboxylic acid amide, -esters, etc. Also the RCOR compound can contain in the beta position to the carbonyl group substituents such as hal nitrile, carboxylic acid amide, -ester. The condensation can be carried out with the named initial compounds without a reaction in the substituted groups taking place.

EMBODIMENTS 66 TO 71

General working rules for platinum metal-phthalocyanine catalysed reduction with $NaBH_4$.

Using $N_2$ 2.7 g (70 mMol) $NaBH_4$ are added to 50 ml EtOH 0.5 g (ca 0.9 mMol) Mpc. To the dark-colored solution or suspension (for $[Pd^IPc]^{\ominus}$: black) is added 10 mMol educt (tables 5 and 6) and is stirred while being water-cooled with pressure compensation at 20° to 25° C. (times in tables 5 and 6). The mixture is neutralized while cooling with ice with 5N HCl (about 10 minutes to the end of the initially strong gas development; pH 4-7), the dark blue deposit is centrifuged (5 minutes at 3000 rpm) off, and the latter is washed with MeOH, whereby the catalyst MPc remains. For reuse the catalyst is washed three more times with water and dried (between 20° and 200° C.). The combined centrifugate is concentrated and the residue is distributed in a suitable pair of solvents such as $H_2O$/ether. With aliphatic amines, the residue is distributed in 1N NaOH/ether. After the concentration of the organic phase dried over $Na_2SO_4$, the products or nonreacted educts are obtained. They are purified in the case of neutral substances by filtering of a solution in hexane/ether, for amines by filtration of a hydrochloric aqueous solution and for amino acids or peptides by filtration of the citric acid solution.

TABLE 2

PdPc catalysed hydrogenations in EtOH, for conditions see example

| No | Educt | Product | Stir Time (h) | Yield % | Comment |
|---|---|---|---|---|---|
| 1 | $C_6H_5-NO_2$ | $C_6H_5-NH_2$ | 21,5 | 92 | — |
| 2 | " | " | 3,5 | 95 | TEA-additive |
| 3 | $p-CH_3-C_6H_4-NO_2$ | $p-CH_3-C_6H_4-NH_2$ | 7,5 | 91 | — |
| 4 | $p-Cl-C_6H_4-NO_2$ | $C_6H_5-NH_2$ | 120 | 100 | — |
| 5 | " | " | 22 | 88 | TEA-additive |
| 6 | " | $p-Cl-C_6H_4-NH_2$ | 36 | 73 | HCl-additive |
| 7 | $m-NO_2-C_6H_4-CO-CH_3$ | $m-NH_2-C_6H_4-CO-CH_3$ | 69 | 100 | — |
| 8 | $m-NO_2-C_6H_4-CH=CH-CO_2Me$ | $m-NH_2-C_6H_4-CH_2-CH_2-CO_2Me$ | 141 | 92 | — |
| 9 | $C_6H_5-CH=CH-NO_2$ | $C_6H_5-CH_2-CH_2-NO_2$ | 384 | 100 | — |
| 10 | $n-C_8H_{17}-NO_2$ | Educt | 140 | (97) | — |
| 11 | $C_6H_5-CH_2-CN$ | " | 824 | (97) | — |
| 12 | " | " | 480 | (100) | TEA-additive |
| 13 | " | $(C_6H_5-CH_2-CH_2)_2NH$ | 20 | 100 | 50 atu, 100° C. |
| 14 | Hexene (1) | Hexane | 4 | — | — |
| 15 | " | " | 8 | — | HCl-additive |
| 16 | " | " | 2,5 | — | Lm: MeOH |
| 17 | " | " | 6,5 | — | Lm: t-BuOH/$H_2O$ (10:1) |
| 18 | " | " | 20 | — | Lm: glacial acetic adic |
| 19 | " | " | 40 | — | Lm: Acetone |
| 20 | " | " | 120 | — | Lm: Acetonitril |
| 21 | " | " | 2 | — | DCHEA-additive |
| 22 | β-Pinene | cis-Pinane | 395 | 71 | TEA-additive |
| | | trans-Pinane | | 29 | |
| 23 | oleic acid | stearic acid | 29 | 99,5 | — |
| 24 | " | " | 12 | 72 | TEA-additive |
| 25 | $C_6H_5-CH=CH-CO_2H$ | $C_6H_5-CH_2-CH_2-CO_2H$ | 6.5 | 98 | — |
| 26 | $C_6H_5-CH=CH-CO_2Et$ | $C_6H_5-CH_2-CH_2-CO_2Et$ | 40 | 99 | Lm: Acetronitril |
| 27 | $C_6H_5-\underset{\underset{CH_2-CH_3}{\vert}}{C}=CH_2$ | $C_6H_5-\underset{\underset{CH_2-CH_3}{\vert}}{CH}-CH_3$ | 24 | 85 | — |
| 28 | Furan | THF | 10 | — | — |
| 29 | $c-C_3H_5-CH_2-OH$ | Educt (initial product) | 100 | (55) | — |
| 30 | $m-Cl-C_6H_4-CO_2H$ | $C_6H_5-CO_2H$ | 429 | 50 | — |
| | | Educt | | (50) | |
| 31 | " | $C_6H_5-CO_2H$ | 22 | 99 | TEA-additive |
| 32 | $o-Cl-C_6H_4-CO_2Et$ | Educt | 125 | (96) | — |
| 33 | " | $C_6H_5-CO_2H$ | 2.5 | 99 | TEA-additive |
| 34 | $o-Cl-C_6H_4-CO_2-CH_2-CH_2-Br$ | Educt | 210 | 92 | — |

TABLE 2-continued

PdPc catalysed hydrogenations in EtOH, for conditions see example

| No | Educt | Product | Stir Time (h) | Yield % | Comment |
|----|-------|---------|---------------|---------|---------|
| 35 | " | $C_6H_5-CO_2-CH_2-CH_2-Br$ | 112 | 67 | TEA-additive |
| 36 | $n-C_{12}H_{25}-Br$ | Educt | 287 | 100 | — |
| 37 | $C_6H_5-CHO$ | $C_6H_5-CH_3$ | 16 | 100 | — |
| 38 | $C_6H_5-CH=CH-CHO$ | $C_6H_5-CH_2-CH_2-CH_2-OH$ | 33 | 80 | Lm: Acetonitril |
| 39 | $C_6H_5-CH(CH_3)-CHO$ | Educt | 22 | (100) | Diethylacetal |
| 40 | $C_6H_5-CH=N-i-C_3H_7$ | $C_6H_5-CH_2-NH-i-C_3H_7$ | 4 | 100 | — |
| 41 | $C_6H_5-CH(CH_3)-CH=N-n-C_4H_9$ | $C_6H_5-CH(CH_3)-CH_2-NH-C_4H_9$ | 27 | 100 | — |
| 42 | 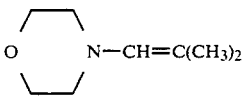 | 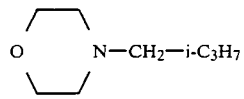 | 4 | 77 | — |
| 43 | $C_6H_5-CH_2-CO_2-CH_2-C_6H_5$ | $C_6H_5-CH_2-CO_2H$ | 12 | 98 | — |
| 44 | " | " | 5 | 66 | TEA-additive |
| 45 | $n-C_8H_{17}-O-CH_2-C_6H_5$ | Educt | 95 | (99) | — |
| 46 | " | " | 144 | (100) | TEA-additive |
| 47 | $C_6H_5-CO-NH-CH_2-C_6H_5$ | " | 110 | (100) | — |
| 48 | " | " | 266 | (97) | TEA-additive |
| 49 | $C_6H_5-COCl$ | " | 260 | (93) | Lm: Acetonitril |
| 50 | $C_6H_5-CH=CH-COCl$ | " | 40 | (94) | " |
| 51 | oleic acid chloride | " | 21,5 | (99) | " |

Abbreviations:
TEA = Triethylamine.
DCHEA = Dicyclohexylethylamine,
THF = Tetrahydrofuran.

TABLE 3

MpC catalysed hydrogenations in EtOH, conditions as in examples

| No. | M | educt | Product | Stir time h | Yield % |
|-----|---|-------|---------|-------------|---------|
| 11 | Pd | $C_6H_5-NO_2$ | $C_6H_5-NH_2$ | 21,5 | 92 |
| 52 | Pt | $C_6H_5-NO_2$ | $C_6H_5-NH_2$ | 180 | 83 |

TABLE 4

Single pot synthesis of amines by reductive amination with $H_2$ PdPc catalysed by aromatic and aliphatic carbonyl compounds, for conditions see example

| No | educt | product | Stir time (h) | Yield (%) |
|----|-------|---------|---------------|-----------|
| 53 | $C_6H_5-CO-CH_3$<br>$NH_3$ | $C_6H_5CH-CH_3$<br>\|<br>$NH_2$ | 307 | 52 |
| 54 | $C_6H_5-CH(CH_3)-CHO$<br>$NH_2-n-C_4H_9$ | $C_6H_5-CH(CH_3)-CH_2NH-n-C_4H_9$ | 28 | 100 |
| 55 | $C_6H_5-CHO$<br>$NH_2-i-C_3H_7$ | $C_6H_5-CH_2-NH-i-C_3H_7$ | 8 | 82 |
| 55a | $CH_3-CO-CO_2H$<br>$n-C_4H_9-NH_2$ | $CH_3$<br>\|<br>$n-C_4H_9-NH-CH-CO_2H$ | 136 | 66 |
| 55b | 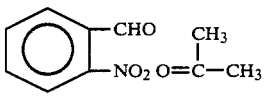 | 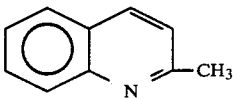 | 120 | 43 |

TABLE 5

PdPc as bifunctional reduction catalyst with controllable reaction specificity in the selective splitting off of protective groups in peptide chemistry, for conditions see example

| No. | Reduction agent | Solvent | Educt[1] | Product | Stir time h | Yield % |
|-----|-----------------|---------|----------|---------|-------------|---------|
| 56 | $H_2$ | EtOH | BEOC—Val—OBzl | BEOC—Val—OH | 22 | 56 |
| 57 | " | " | TCBOC—Val—OMe | Educt | 20 | (97) |
| 58 | " | " | Z-Ala—Val—OBzl | Z-Ala—Val—OH | 75 | 72 |
| 59 | " | t-BuOH/$H_2O$ | TCBOC—Val—OBzl | TCBOC—Val—OH | 46 | 85 |

TABLE 5-continued

PdPc as bifunctional reduction catalyst with controllable reaction specificity in the selective splitting off of protective groups in peptide chemistry, for conditions see example

| No. | Reduction agent | Solvent | Educt[1] | Product | Stir time h | Yield % |
|---|---|---|---|---|---|---|
| 60 | " | (10:1) | TCBOC—Aib—Ala—OBzl | TCBOC—Aib—Ala—OH | 6 | 92 |
| 61 | " | " | TCBOC—Val—Aib—OBzl | TCBOC—Val—Aib—OH | 135 | 89 |
| 62 | " | " | TCBOC—Aib—Pro—OBzl | TCBOC—Aib—Pro—OH | 44 | 67 |
| 63 | " | " | TCBOC—Gly—Leu—OBzl | TCBOC—Gly—Leu—OH | 68 | 73 |
| 64 | " | acetic acid | BOC—Gly—Leu—N— —N—Val—NH—CH$_2$—Fc \| CH$_2$—Fc | Educt | 70 | (89) initial product |
| 65 | " | EtOH | " | " | 70 | (98) |
| 66 | NaBH$_4$ | " | " | " | 30 | (100) |
| 67 | " | " | TCBOC—Phe—OtBu | H—Phe—OtBu | 18 | 82 |
| 68 | " | " | TCBOC—Val—OBzl | H—Val—OBzl | 20 | 81 |

[1]Usual abbreviations in peptide chemistry, see "E. Wunsch, Houben-Weyl, Vol. 15, Thieme Stuttgart, 1974," TCBOC = 2,2,2-trichloro-tert.-butyloxycarbonyl; Fc = ferrocenyl

TABLE 6

PdPc catalysed reduction with NaBH$_4$ in EtOH, for conditions see examples

| No. | Educt | Product | Stir time (h) | Yield (%) |
|---|---|---|---|---|
| 69 | p-Cl—C$_6$H$_5$NO$_2$ | p-Cl—C$_6$H$_5$NH$_2$ | 2 | 80 |
| 70 | " | " | 120 | 98 |
| 71 | C$_6$H$_5$CH=CHCO$_2$Et | C$_6$H$_5$CH$_2$CH$_2$CO$_2$Et | 0,5 | 93 |

I claim:

1. Process for the reduction of reducible groups characterized in that an effective amount of a platinum-metal-phthalocyanine of the following formula is used as the catalyst:

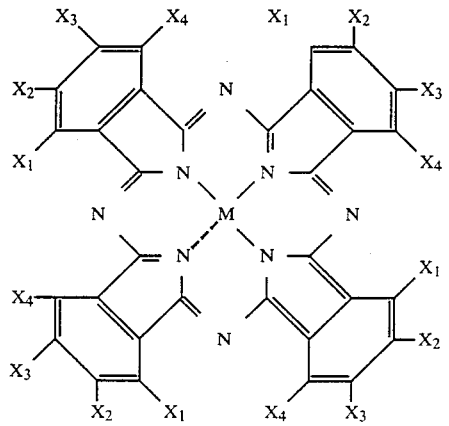

where M is a metal of the platinum metal series, $X^{1-4}$ is halogen, cyano or optionally other substituents with —I— effect, alkyl or aryl, while $X^{2-3}$ can also be components of an annellated ring system or poly-Pc-structure, and $X^{1-4}$ can independently substitute one or more of the benzoid rings, for a selective reduction at a temperature of 0° C. to 200° C. with an effective amount of hydrogen on [MPc], with M having a formal charge $z \geq 2$ to reduce the functional groups C=C, C=N, aromatic NO$_2$, aromatic CH=O, benzyl esters and aromatic halogen compounds, the latter being only reduced in a basic medium.

2. Process for the reduction of reducible groups characterized in that an effective amount of a platinum-metal-phthalocyanine of the following formula is used as the catalyst:

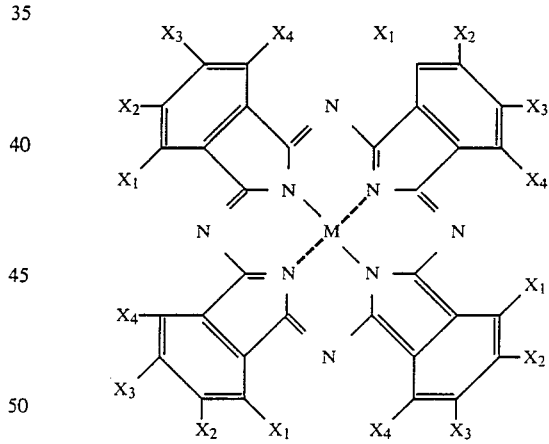

where M is a metal of the platinum metal series, $X^{1-4}$ is halogen, cyano or optionally other substituents with —I— effect, alkyl or aryl, while $X^{2-3}$ can also be components of an annellated ring system or poly-Pc-structure, and $X^{1-4}$ can independently substitute one or more of the benzoid rings, for a selective reduction at a temperature of 0° C. to 200° C. with an effective amount of a suitable reduction agent on [MPc]$^-$ with M having a formal charge $z \leq 1$ to reduce the functional groups C=C, C=N, C≡N, C=O, NO$_2$, alkyl halogenides and carbonic acid halogenides is obtained.

3. Process for the removal of reducible protecting groups from a protected amino acid(s) or oligo- and polypeptide(s) characterized in that an effective amount of a platinum-metal-phthalocyanine of the following formula is used as the catalyst:

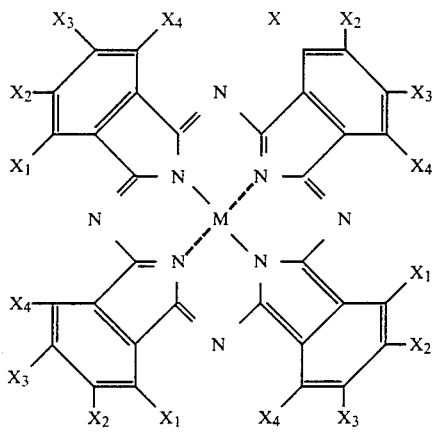

where M is a metal of the platinum metal series, $X^{1-4}$ is halogen, cyano or optionally other substituents with —I— effect, alkyl or aryl, while $X^{2-3}$ can also be components of an annellated ring system or poly-Pc-structure, and $X^{1-4}$ can independently substitute one or more of the benzoid rings, for a selective reduction at a temperature of 0° C. to 200° C. with an effective amount of hydrogen on [MPc], with M having a formal charge $z \geq 2$ to reduce the functional groups C=C, C=N, aromatic $NO_2$, aromatic CH=O, benzyl esters and aromatic halogen compounds, the latter being only reduced in a basic medium.

4. Process for the removal of reducible protecting groups from a protected amino acid(s) or oligo- and polypeptide(s) characterized in that an effective amount of a platinum-metal phthalocyanine of the following formula is used as the catalyst:

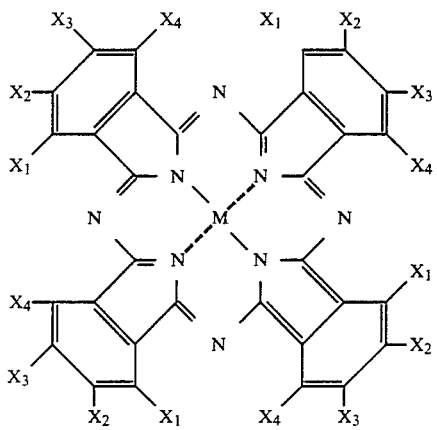

where M is a metal of the platinum metal series, $X^{1-4}$ is halogen, cyano or optionally other substituents with —I— effect, alkyl or aryl, while $X^{2-3}$ can also be components of an annellated ring system or poly-Pc-structure, and $X^{1-4}$ can independently substitute one or more of the benzoid rings, for a selective reduction at a temperature of 0° C. to 200° C. with an effective amount of a suitable reduction agent on [Mpc]$^-$ with M having a formal charge $z \leq 1$ to reduce the functional groups C=C, C=N, C≡N, C=O, $NO_2$, alkyl halogenides, especially by the reductive fragmentation of β-halogenalkyl groups, and carbonic acid halogenides is obtained.

5. Process according to claim 1 or 2, characterized in that the change of the oxidation phase z of the metal from $z \geq 2$ to $z \leq 1$ makes the reaction specificity of the MPc complex controllable.

6. Process according to claim 1 or 2, characterized in that M is palladium.

7. Process according to claim 1, characterized in that $H_2$ is used as the reduction agent in a low temperature range without pressure.

8. Process according to claim 2, characterized in that together with [MPc]$^\ominus$ $NaBH_4$ is used as the reduction agent.

9. Process according to claim 1 or 2, characterized in that the reduction is greatly speeded by the addition of a free base.

10. Process according to claim 1 characterized in that the reduction reaction is performed selectively in the presence of an acid-halogen group, while the latter remains unaffected during the reduction catalysis with $H_2$.

11. Process according to claim 1 characterized in that the reduction catalysis is carried out selectively in the presence of an optionally geminal polyhalogenated alkylhalide group, whereby the latter remains unaffected during the reduction reaction with $H_2$.

12. Process according to claim 1 or 2 characterized in that the reduction reaction is selectively carried out in the presence of a benzylamine or 1-ferrocenylalkylamino group whereby the latter remain unaffected.

13. Process according to claim 1 or 2 characterized in that the reduction catalysis is selectively performed in the presence of a benzyl ether- or 1-ferrocenylalkylether group, while the latter remain unaffected.

14. Process according to claim 1 or 2 characterized in that the reduction catalysis is selectively performed in the presence of a benzyl amide- or 1-ferrocenylalkylamide group, while the latter remain unaffected.

15. Process according to claim 1 characterized in that the optionally substituted benzyl- or benzyloxycarbonyl groups are selectively hydrogenolytically split off in the presence of and maintaining easily reducible aromatic or heteroaromatic compounds.

16. Process according to claim 1 characterized in that the optionally substituted benzyl ester group is selectively hydrogenolysed in the presence of and maintaining optionally geminal polyhalogenised alkyl halide groups, especially the 2,2,2-tri-chloro-tert.-butyloxycarbonyl residue.

17. Process according to claim 2 characterized in that β-halogenalkyl residues, especially the 2,2,2-tri-chloro-tert.-butyl residue and the 2,2,2-tri-chloro-tert.-butyloxycarbonyl residue are split off selectively from heteroatoms, e.g. O, N, or S, by reductive fragmentation with $NaBH_4$.

18. Process according to claim 2 characterised in that β-halogenalkyl residues, especially the 2,2,2-tri-chloro-tert.-butyl residue and the 2,2,2-tri-chloro-tert.-butyloxycarbonyl residue are split off selectively beside a benzyl ester.

19. Process according to claim 1 characterized in that in the case of MPc-catalyzed reduction reaction with $H_2$ by appropriate selection of the pH value aromatic halides are either quickly hydrogenolized by selective addition of a base, or they remain unaffected by addition of an acid, without markedly influencing the reduction reaction of another functional group.

20. The process according to claim 3 wherein optionally substituted benzyl or benzyloxycarbonyl groups are hydrogenolytically split from peptides which contain aromatic groups such as especially the amino acids, histidine, tryptophane, tyrosine, phenyl glycine, p-hydroxyphenylglycine or phenylalaline.

21. The process according to claim 3 or 4 wherein amino acids or oligo- and polypeptides on the amino functions are protected by 2,2,2-tri-chloro-tert.-butyloxycarbonyl radicals and on the carboxyl functions by benzyl radicals.

22. The process according to claims 3 or 4 wherein there is selective splitting off of β-halogenalkyl radicals, especially 2,2,2-tri-chloro-tert.-butyloxycarbonyl radical, with $NaBH_4$, on $[Pd^I Pc]^\ominus$ or of optionally substituted benzyl or benzyloxycarbonyl radicals with $H_2$ on $Pd^{II}Pc$, secondary or tertiary 1-ferrocenyalkylamide groups are maintained.

23. The process according to claims 3 or 4 wherein the hexapeptide His-His-Trp-His-Trp-His is prepared.

24. The process according to claim 3 or 4 characterized in that the metal M is selected from the group consisting of Ru, Os, Rh, Ir, Pd and Pt.

25. The process according to claim 3 or 4 characterized in that the metal M is Pd.

* * * * *